United States Patent [19]

Hitzman

[11] Patent Number: 4,540,052

[45] Date of Patent: Sep. 10, 1985

[54] GENERATION OF MICROORGANISM CONTROL COMPOSITION AND USE THEREOF

[75] Inventor: Donald O. Hitzman, Bartlesville, Okla.

[73] Assignee: Phillips Petroleum Company, Bartlesville, Okla.

[21] Appl. No.: 506,187

[22] Filed: Jun. 21, 1983

Related U.S. Application Data

[63] Continuation-in-part of Ser. No. 363,738, Mar. 30, 1982, abandoned.

[51] Int. Cl.³ .................... E21B 43/20; E21B 43/24; C02F 1/50; C01B 15/024
[52] U.S. Cl. .................... 166/303; 166/59; 166/269; 166/275; 210/764; 422/28; 423/591
[58] Field of Search .................. 210/759, 764, 774; 423/580, 584, 587, 591; 166/257, 260, 261, 310, 311, 312, 303, 59, 275, 246; 422/28, 29, 36

[56] References Cited

U.S. PATENT DOCUMENTS

| Re. 15,789 | 3/1924 | Bibb | 422/36 |
|---|---|---|---|
| 2,105,835 | 1/1938 | Krause | 210/759 X |
| 2,987,475 | 6/1961 | Legator | 166/275 |
| 3,104,702 | 9/1963 | Gaskell et al. | 166/306 |
| 3,228,829 | 1/1966 | Wolf et al. | 210/764 |
| 3,514,278 | 5/1970 | Brink, Jr. | 210/764 X |
| 4,376,094 | 3/1983 | Munzenmaier et al. | 422/36 |

FOREIGN PATENT DOCUMENTS 52522 12/1941 Netherlands .

OTHER PUBLICATIONS

Kibbel, Jr. et al., "An Evaluation of Peroxides as Waterflood Bactericides", Producers Monthly, vol. 27, No. 12, Dec. 1963, pp. 16-20.

Primary Examiner—George A. Suchfield
Attorney, Agent, or Firm—C. F. Steininger

[57] ABSTRACT

In accordance with the present invention, microorganisms are controlled in a body of fluid, particularly an aqueous fluid containing such microorganisms, by burning a hydrogen-containing fuel in the presence of an oxidizing agent under conditions sufficient to produce partial oxidation products, containing significant amounts of at least one compound capable of controlling microorganisms, such as hydrogen peroxide and aldehydes controlling the burning step to prevent significant decomposition of the thus produced partial oxidation products and the formation of products of complete combustion therefrom by controlling the burning step by selecting at least one of the type of hydrogen-containing fuel, the fuel/oxidizing agent equivalence ratio, the temperature, the pressure and the residence time, preferably the residence time by introducing a quench medium, particularly water, into the partial oxidation products, to produce an effluent containing said partial oxidation products containing including at least one compound capable of controlling microorganisms and contacting the body of fluid with the effluent.

In one specific aspect of the present invention, all or part of the body of fluid to be treated is utilized as a quench medium to terminate the burning.

In yet another specific aspect of the present invention, oil is displaced from an oil-bearing subsurface earth formation with water by generating the microorganism control material containing effluent as stated above, and utilizing the thus generated effluent to treat the water.

38 Claims, 5 Drawing Figures

GENERATION OF MICROORGANISM CONTROL COMPOSITION AND USE THEREOF

This application is a continuation-in-part of Application Ser. No. 363,738, now abandoned, filed Mar. 30, 1982 by the present inventor.

BACKGROUND OF THE INVENTION

The present invention relates to the generation of microorganism control compositions and the use thereof. In a more specific aspect, the present invention relates to a method of treating a body of fluid containing microorganisms in order to control such microorganisms.

In a number of industrial and municipal operations, the presence of microorganisms in bodies of fluid cause innumerable problems. For example, the growth of microorganisms in bodies of fluid often results in the plugging of structures into which or through which such fluid is to be passed, accumulation in the structures and thus reduction of fluid flow and, to the extent that small amounts of water are present, serious corrosion problems. Accordingly, it is common practice to employ microorganism control compositions to kill the microorganisms, or at least, prevent their rate of growth. Numerous microorganism control compositions are known for this purpose. However, such known microorganism control compositions, in many cases, are prohibitively costly to manufacture and are not available to remote locations where needed and are fraught with numerous problems in the handling and use thereof.

A particularly effective microorganism control material is hydrogen peroxide. However, the problems associated with the manufacture and use of hydrogen peroxide severely limit its use, particularly for the treatment of large bodies of fluid. While pure solutions of hydrogen peroxide, completely free of contaminants, are highly stable, such pure solutions are expensive and their purity almost impossible to maintain. On the other hand, concentrated solutions are highly toxic and strong irritants. In addition, in solution, hydrogen peroxide decomposes into water and oxygen, which decomposition is accelerated by the presence of impurities. Since solid hydrogen peroxide is explosive, there is always the danger of fire and explosion in the event attempts are made to utilize the same in this form, as well as in solution.

As previously indicated, the expense of utilizing hydrogen peroxide is a major factor. This is due to a complexity of commercial methods for manufacture and separation of the hydrogen peroxide. One common method is the autooxidation of an alkylanthrahydroquinone, such as the 2-ethyl derivative, in a cyclic continuous process in which the quinone formed in the oxidation step is reduced to the starting material by hydrogen in the presence of a supported paladium catalyst. A second technique involves electrolytic processes in which aqueous sulfuric acid or acidic ammonium bisulfate are converted electrolytically to the peroxybisulfate which is then hydrolyzed to form hydrogen peroxide. A third method is the autooxidation of isopropyl alcohol. Of these techniques, the first mentioned is the most widely utilized. It is also known that hydrogen peroxide can be produced as a by-product by the autooxidation of paraffinic hydrocarbons, such as propane, to produce olefins. Efforts have been made to maximize the production of hydrogen peroxide in this type reaction. However, no known commerical process utilizes this type of reaction and, hence, it has remained a laboratory curiosity.

Another effective microorganism control material is glutaraldehyde. This material is widely used where large bodies of fluids are to be treated, such as flood waters, for the recovery of oil, due primarily to its lower cost than other microorganism control materials, its effectiveness is relatively small amounts, its nonflammability and the ability to handle the same in relatively high concentrations. However, glutaraldehyde is toxic and an irritant and, therefore, reasonable care must be taken in the manufacture and handling of the same. Other aldehydes which are effective microorganism control materials include formaldehyde and aceteldehyde. These materials are also toxic and an irritant and, thus, care in the manufacture and handling is necessary and formaldehyde is a gas and polymerizes readily, thus, requiring the addition of inhibitors, such as methanol, to aqueous solutions but these materials have lower fire risks than hydrogen peroxide or glutaraldehyde. Ketones, such as acetone, and ethers, such as propylene oxide, esters, etc. also act as microorganism control materials. However, both acetone and propylene oxide are highly flammable but are moderately toxic and irritant. The above-mentioned disadvantages of the aldehydes, ketones, ethers and esters thus require care in the manufacture and handling of the same and must be transported as solutions. For example, glutaraldehyde is available in aqueous solutions of 50% and 25% by volume and formaldehyde is commercially available in concentrations of 37% to 50% in an aqueous solution containing up to 15% methanol as a polymerization inhibitor. Accordingly, while glutaraldehyde is effective as a microorganism control material in concentrations of about 10 to 50 parts per million by volume, it is necessary to transport substantial amounts of water along with the active agent. This is particularly troublesome where the material is to be utilized in large volumes, as in the treatment of waterflood waters, and particularly where it is to be utilized at remote locations, such as offshore production platforms.

Summarily, as previously indicated, the utilization of microorganism control materials, particularly hydrogen peroxide and aldehydes, in the treatment of large bodies of fluid becomes a rather expensive proposition since large amounts of microorganisms control materials are necessary. For example, in the treatment of water utilized for the displacement of oil in oil field operations, the treatment of pipeline slurries flowing through a pipeline and other industrial operations the cost becomes a significant factor and the availability of microorganism control materials at the location where needed further emphasize the problems in their use. It is common practice in the recovery of oil to inject water into an oil bearing formation to displace additional amounts of oil after the natural drive energy of the reservoir has dissipated. However, the presence of microorganisms, particularly sulfate-reducing bacteria, in the flood water causes serious problems of plugging of the oil bearing formation and corrosion of injection and downhole equipment. Consequently, it is necessary in such cases to kill the microorganisms, or at least retard their growth, to prevent or reduce these problems.

SUMMARY OF THE INVENTION

It is therefore, an object of the present invention to provide an improved method of microorganism control material generation and use which overcomes the above and other problems of the prior art.

Another object of the present invention is to provide an improved method of microorganism control material generation and use which significantly reduces the cost of such use.

Another and further object of the present invention is to provide an improved method of microorganism control material generation and use wherein the microorganism control material can be generated at comparatively low cost.

Yet another object of the present invention is to provide an improved method of microorganism control material generation and use in which the microorganism control material can be generated at the location at which it is to be used.

Another and further object of the present invention is to provide an improved method of microorganism control material generation and use adapted to continuously produce the microorganism control material.

A further object of the present invention is to provide an improved method of microorganism control material generation and use in which the microorganism control material can be generated in an essentially unattended operation.

A still further object of the present invention is to provide an improved method of microorganism control material generation and use in which the microorganism control material can be generated in a continuous manner and in an essentially unattended operation.

Another object of the present invention is to provide an improved method of microorganism control material generation and use which utilizes readily available and/or relatively inexpensive starting materials, which are in many cases available at the location of use.

Another object of the present invention is to provide an improved method of microorganism control material generation and use in which the body of fluid to be treated is simultaneously treated during the generation of the microorganism control material.

Yet another object of the present invention is to provide an improved method of microorganism control material generation and use in which all of the products can be utilized without separation.

An additional object of the present invention is to provide an improved method of microorganism control material generation and use in which the heat of reaction aids in the activity of the microorganism control material.

Another and further object of the present invention is to provide an improved method of microorganism control material generation and use in which the microorganism control material generation is carried out at an elevated pressure and such elevated pressure aids in the microorganism control material use.

A further object of the present invention is to provide an improved method for the generation of hydrogen peroxide, aldehydes, ketones, ethers, esters and other partial oxidation products and their use as a microorganism control material.

A still further object of the present invention is to provide an improved method for the generation of hydrogen peroxide, aldehydes, ketones, ethers, esters and other partial oxidations products and others and their use as a microorganism control material which substantially reduces the cost thereof.

Another further object of the present invention is to provide an improved method for the generation of hydrogen peroxide, aldehydes, ketones, ethers, esters and and other partial oxidation products which overcomes the prior art problems of handling the same.

Another object of the present invention is to provide an improved method of generating microorganism control materials which overcomes the problems of the decomposition of the same during use.

Another and further object of the present invention is to provide an improved method of displacing oil from subterranean oil-bearing formations.

Yet another object of the present invention is to provide an improved method of displacing oil from oil-bearing subsurface formations with water, in which the water is simultaneously treated with a microorganism control material.

Another and further object of the present invention is to provide an improved method of displacing oil from oil-bearing subsurface formations with water, in which microorganisms present in the water are controlled and which overcomes the above-mentioned and other problems in the production, handling and use of such microorganism control materials.

Yet another object of the present invention is to provide an improved method of displacing oil from an oil-bearing subsurface formation with water in which microorganisms present in the water are controlled with hydrogen peroxide, aldehydes, ketones, ethers and/or esters, while overcoming the above-mentioned and other problems in the manufacture, handling and use of such microorganism control materials.

These and other objects of the present invention will be apparent from the following description.

In accordance with the present invention, microorganisms are controlled in a body of fluid, particularly an aqueous fluid containing such microorganisms, by burning a hydrogen-containing fuel in the presence of an oxidizing agent under conditions sufficient to produce partial oxidation products, containing significant amounts of at least one compound capable of controlling microorganisms, such as hydrogen peroxide and aldehydes controlling the burning step to prevent significant decomposition of the thus produced partial oxidation products and the formation of products of complete combustion therefrom by controlling the burning step by selecting at least one of the type of hydrogen-containing fuel, the fuel/oxidizing agent equivalence ratio, the temperaure, the pressure and the residence time, preferably the residence time by introducing a quench medium, particularly water, into the partial oxidation products, to produce an effluent containing said partial oxidation products containing including at least one compound capable of controlling microorganism and contacting the body of fluid with the effluent.

In one specific aspect of the present invention, all or part of the body of fluid to be treated is utilized as a quench medium to terminate the burning.

In yet another specific aspect of the present invention, oil is displaced from an oil-bearing subsurface earth formation with water by generating the microorganism control material containing effluent as stated above, and utilizing the thus generated effluent to treat the water.

DETAILED DESCRIPTION OF THE PREFERRED EMBODIMENTS

Figure 1:
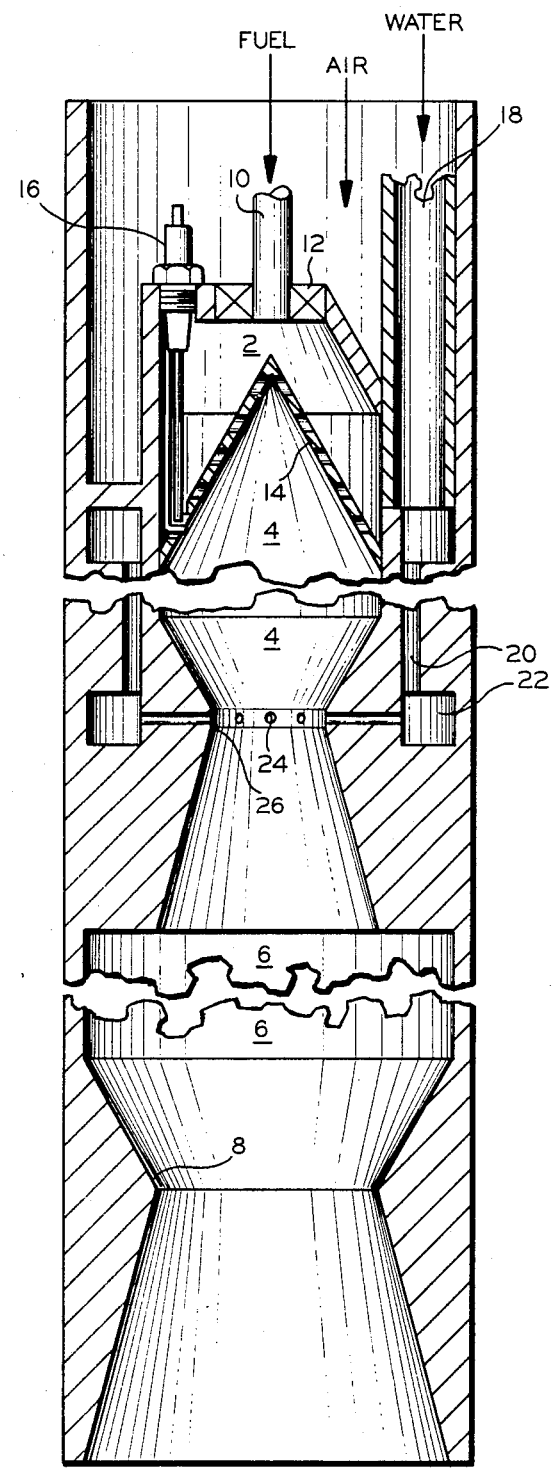
FIG. 1 of the drawings is a schematic view, partially in cross section, of a microorganism control material generator, useful in accordance with the present invention.
Figure 2:
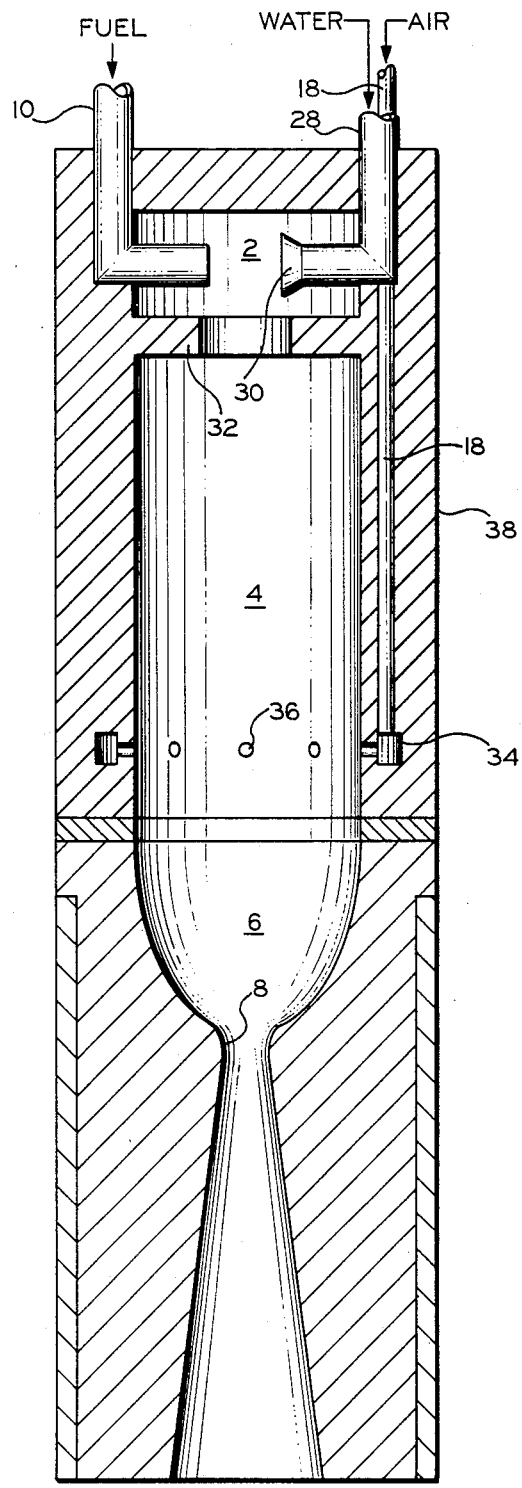
FIG. 2 is a schematic view, partially in cross section, of a modification of the generator of FIG. 1.

When used herein, the term "body of fluid" is meant to include any confined body of fluid such as fluid held in a container, a pond or the like, as well as, a flowing body of such fluid in a pipeline, stream or the like, and including aqueous fluids, such as water, and non-aqueous fluids containing water, as well as non-aqueous fluids such as oil, etc.

The terms antiseptic and disinfectant, as well as the similar terms bactericide, bacteriostat, germicide, virucide and sterilizing agent, are often used synonomously. Strictly speaking, antiseptic is meant to include materials which inhibit the growth of microorganisms without necessarily destroying them, as distinguished from a disinfectant which kills microorganisms. Accordingly, the terms "control" and "controlling", when utilized with respect to microorganisms will be utilized herein to refer to prevention of the growth of microorganisms and/or the killing of microorganisms and the phrases "microorganism control material" and "microorganism control materials" will be utilized herein to refer to compounds and/or mixtures thereof which are effective in preventing the growth of microorganisms and/or in killing microorganisms.

The term "hydrocarbyl fuel" when utilized herein is meant to include normally gaseous, normally liquid and/or normally solid fuels containing hydrogen and carbon and capable of oxidation, combustion or burning.

The term "hydrogen-containing fuel" is meant to include normally gaseous, normally liquid and/or normally solid fuels containing hydrogen capable of producing hydrogen atoms or perhydroxal radicals upon oxidation, combustion or burning of the fuel.

The phrases "complete oxidation", "complete combustion" and "complete oxidation" are meant to include the oxidation, combustion or burning of a hydrogen-containing fuel or a hydrocarbyl fuel in the presence of an oxidizing agent to produce an effluent comprising carbon dioxide and water, in some cases carbon monoxide and nitrogen, and/or unburned or unoxidized fuel and free of significant amounts of intermediate oxygen-containing products formed during oxidation, combustion or burning of a fuel to such ultimate products.

The phrases "partial oxidation", "partial combustion" and "partial burning" are utilized herein to refer to the oxidation, combustion or burning of a hydrogen-containing fuel or a hydrocarbyl fuel under conditions to produce an effluent containing significant amounts of oxygen-containing intermediate products, including without limitation, hydrogen peroxide, aldehydes, ketones, ethers, esters, alcohols, and the like which are formed during an intermediate stage of oxidation, combustion or burning prior to the formation of the products of complete combustion referred to above and, more specifically carbon dioxide, water, in some cases, carbon monoxide and nitrogen, and/or unburned fuel. The products of such partial oxidation, combustion or burning are referred to as "partial oxidation products".

The term "oxidizing agent" is meant to include air, oxygen or other oxygen-containing materials capable of supporting oxidation, combustion or burning of a fuel.

The term "quench fluid" is meant to include air, water, mixtures thereof, or other gases, liquids or vapors adapted to terminate the combustion or burning of a fuel and/or cool the partial oxidation products.

The terms "fuel-air equivalence ratio", "equivalence ratio" and the symbol "$\phi$" are employed herein to refer to the ratio of the fuel flow (fuel available) to the fuel required per stoichoimetric combustion with the air available. Stated in another way, said equivalence ratio is the ratio of the actual fuel-air mixture to the stoichoimetric fuel-air mixture. For example, an equivalence ratio 1.5 means the fuel-air mixture is fuel-rich and contains 1.5 times as much fuel as a stoichoimetric mixture and a equivalence ratio of 0.5 means the fuel-air mixture is fuel-lean and contains 0.5 times as much fuel as a stoichoimetric mixture. Obviously, a stoichoimetric mixture by this definition has an equivalence ratio of 1.0.

During the course of combustion of any hydrocarbyl fuel or hydrogen-containing fuel, a large number of intermediate reactions occur prior to attainment of complete combustion of the fuel to essentially carbon dioxide, water and, to the extent air is utilized as an oxidizing agent, nitrogen. During the course of such combustion, certain reactions such as cracking, dehydrogenation, hydrogenation and the like occur, resulting in intermediate products of combustion essentially free of oxygen, such as other hydrocarbons and carbon. However in the context of the present application such oxygen-free intermediate products do not function as microorganism control agents and accordingly are considered inert. On the other hand, a wide variety of other reactions occur prior to complete combustion of the fuel by combination of the original components of the fuel and/or the above-mentioned oxygen-free intermediate products with an oxidizing agent to produce a wide variety of oxygen-containing, partial oxidation products or intermediate products. For example hydrogen peroxide, aldehydes, ketones, ethers, esthers, alcohols, organic peroxides and the like. With the exception of alcohols, all of these oxygen-containing, partial oxidation products are effective to a greater or lesser extent as microorganism control agents. Ordinarily, unless the oxidation combustion or burning is controlled in some manner, the ultimate effluent will be essentially products of complete combustion, including carbon dioxide, water, in some case carbon monoxide, where air is the oxidizing agent, nitrogen, in some cases unburned fuels and intermediate products, such as carbon and hydrocarbons and in some cases excess oxidizing agents and containing insignificant amounts of oxygen-containing, intermediate products or oxygen-containing, partial oxidation products. On the other hand, in accordance with the present invention, partial oxidation can be carried out to produce effluents containing significant amounts of oxygen-containing, intermediate products or oxygen-containing, partial oxidation products by controlling at least one of fuel air equivalence ratio, the temperature, the residence time, the type of hydrocarbon fuel and the pressure during the combustion process. It should be recognized at this point that these conditions are interrelated and, in certain cases, control of one of these conditions results in control of one or more of the other conditions.

Within the realm of the control of the fuel-oxygen equivalence ratio, combustion can be carried out under fuel-rich conditions, that is at an equivalance ratio above 1.0, at the stoichiometric ratio, that is an equivalence ratio of 1.0, or fuel-lean and oxygen-containing, partial oxidation products can be produced under all of these conditions. Conbustion of a fuel-rich mixture will thus produce hydrogen peroxide, aldehydes and other oxygen-containing, partial oxidation products in varying amounts depending upon the other conditions employed. Since there is an excess of fuel when equilibrium is reached, the effluent will contain significant amounts of oxygen-containing, partial oxidation products, such as hydrogen peroxide, aldehydes and other oxygen-containing materials. However, hydrogen peroxide is highly unstable and it is, therefore, necessary to limit the residence time, as hereinafter pointed out, to a time less than that necessary to reach equilibrium. While aldehydes and other oxygen-containing materials are more stable than the hydrogen peroxide and can be found in significant quantities in a fuel-rich combustion effluent, they are somewhat less stable than products of complete combustion, such as carbon dioxide and water and, therefore, in order to maximize the production of these oxygen-containing, partial oxidation products, the residence time should also be less than that necessary for reaching equilibrium. On the other hand, where a stoichiometric mixture or a fuel-lean mixture (excess oxygen) is burned, products of complete combustion will be present when equilibrium is reached and, accordingly, it is necessary to limit the residence time to a residence time less than that necessary to reach equilibrium. It is also to be recognized, in this connection, that excess fuel also acts as a diluent or essentially inert material and thus to some extent moderates the temperature.

Limitation of the burning to partial oxidation or partial combustion, as opposed to complete oxidation or combustion, can also be controlled to a certain extent by controlling the combustion temperature. Within the normal deflagration, detonation or explosive range, where the combustion is self sustaining, the temperature may be a high temperature or a low temperature. Higher temperatures can, of course, be attained by preheating the fuel and/or or oxidizing agent, controlling loss of heat by radiation from the flame, etc. It should be recognized here that such preheating is necessary in some cases, particularly where a heavy liquid fuel is to be utilized, since such preheating will aid in mixing of the fuel and the oxidizing agent. Lower temperatures can be attained by diluting the fuel-oxygen mixture, as with excess hydrocarbons as pointed out above, inert materals such as nitrogen, excess oxidizing agent, water and the like. In the case of water, low temperature combustion can be carried out be dispersing or dissolving a fuel in water and simply adding the oxidizing agent to the mixture. This is often referred to as "wet oxidation" and is capable of producing oxygen-containing, partial oxidation products. While wet oxidation is capable of utilizing a wide variety of fuels, particularly waste materials, it is has certain limitations which limit its use in accordance with the present invention. While operating at a low temperature, a high pressure must be maintained. Consequently, when carried out at the surface of the earth, expensive, autoclave-type reactors must be employed. In addition, extremely long residence times, for example from one to five hours are necessary, thus further limiting the use of this process to a certain extent. However, in accordance with the present invention, as hereinafter pointed out, these disadvantages can be overcome by carrying out wet oxidation or wet combustion in a wellbore and subsequently injection of the effluent containing microorgansim control materials into a subsurface earth formation. Lower temperatures can also be attained by indirect heat exchange with a cooling fluid such as water, removing heat radiated by the flame, as by carrying out the reaction in a metallic combustion zone cooled by water, air or the like, etc. In any event, operating at lower temperatures increases the production of oxygen-containing, partial oxidation products to the extent that it reduces or delays the breakdown of such partial oxidation products and extends the residence time for complete combustion. However, again, to maximize the production of oxygen-containing, partial oxidation products, the residence time should be controlled whether high or low temperature combustion is carried out.

The type of hydrocarbon, that is whether saturated, unsaturated, aromatic, etc., as well as the molecular weight of the hydrocarbon fuel, also has an effect upon the production of partial oxidation products, as opposed to products of complete combustion. Therefore, selective use of the fuel can also be utilized to control combustion to produce partial oxidation products.

Pressure control also has an effect upon the production of oxygen-containing, partial oxidation products and thus favor these materials as opposed to products of complete combustion. For example, at a high pressure the ignition temperature of the fuel is lowered and, to the extent liquid or solid fuels are utilized, aids in mixing and, again, more rapid combustion. This, of course, also effects the residence time which can be utilized.

As is apparent from the above, the primary factor, in carrying out partial oxidation to produce oxygen-containing, partial oxidation products, in accordance with the present invention, is control of the residence time. Consequently, in most cases, it is necessary to control the residence time to one below that necessary to reach equilibrium and/or complete combustion and, in the remaining cases, it is highly desirable to do so in order to maximize the production of oxygen-containing, partial oxidation products, which are useful as microorganism control materials. Control of the residence time can be accomplished by cooling. However, it is preferred that the residence time be controlled by rapidly terminating the combustion or rapidly quenching by injecting a quench fluid into the flame front. Such rapid termination of the combustion or rapid quenching is described in detail hereinafter, particularly with reference to the drawings.

Control of the above-mentioned conditions can also be utilized to control the product mix of the oxygen-containing, partial oxidation products. In a broad sense, severe conditions favor the production of hydrogen peroxide, mild conditions favor the production of alcohols, peroxides, ketones, ethers, esters and acids and intermediate conditions favor the production of aldehydes. Further, a fuel-lean equivalence ratio favors the production of hydrogen peroxide, while a stoichiometric or fuel-rich equivalence ratio will favor the production of aldehydes and other oxygen-containing partial oxidation products. Higher temperatures favor the production of hydrogen peroxide whereas the lower temperatures favor the production of aldehydes and other oxygen-containing, partial oxidation products. In the realm of the control of the fuel type, saturated hydrocarbon fuels will generally result in the production of more hydrogen peroxide, whereas unsaturated hydrocarbons increase the production of aldehydes and other oxygen-containing, partial oxidation products. The higher pressures favor the production of hydrogen peroxide while the lower pressures favor production of aldehydes and other oxygen-containing partial oxidation products. Finally, the residence time also controls the product mix to the extent that, in general, shorter residence times result in the production of greater amounts of hydrogen peroxide while longer residence times result in the production of large amounts of aldehydes and other oxygen-containing partial combustion products.

Since, as is apparent from the above, the quantity of oxygen-containing, partial combustion products and the quantities of individual oxygen-containing partial products to be produced, in accordance with the present invention, will vary in accordance with the nature of the fuel utilized, the nature of the microorganism-containing fluid to be treated and other operational factors, it is not possible to set forth specific limits herein. However, one skilled in the combustion art can determine the proper limits by laboratory tests in a combustor of the character hereinafter described while varying individual conditions until significant amounts of oxygen-containing, partial oxidation products are produced of the desired type and quantity sufficient to control microorganisms contained in the body of fluid to be treated.

In addition to the above variations, partial oxidation, in accordance with the present invention, can be carried out as a high intensity-type combustion or low intensity-type combustion. As generally understood in the art, high intensity combustion is combustion in which the fuel and oxidizing agent are premixed or nearly instantaneously mixed in the reactor and thus, combustion approaching that in a well stirred reactor takes place. By contrast, low intensity combustion is akin to combustion in a large furnace where the air and fuel are not premixed or are not mixed essentially instantaneously but are mixed by diffusion. In accordance with the present invention, high intensity combustion is preferred. Accordingly, in order to illustrate the practice of the present invention, such high intensity partial combustion will be described for production of oxygen-containing, partial oxidation products, wherein the amount of hydrogen peroxide is maximized.

As previously indicated, hydrogen peroxide is a very effective biocide for killing microorganisms present in a wide variety of fluids, and particularly, in aqueous fluids.

Therefore, the present invention provides an efficient, effective and economical means of generating hydrogen peroxide, which overcomes the problems of the prior art in the utilization of hydrogen peroxide, and utilizing the thus produced hydrogen peroxide to control microorganisms in a wide variety of fluids. This is accomplished by burning a hydrogen-containing fuel in the presence of an oxidizing agent under conditions sufficient to produce a flame front containing significant amounts of hydrogen peroxide. The hydrogen-containing fuel may include any normally gaseous fuels, such as methane, ethane, propane, butane, etc., particularly natural gas, normally liquid fuels, including various petroleum fractions, diesel fuels, fuel oils, crude oils, alcohol, etc., as well as normally solid fuels, preferably ashless fuels, such as, asphaltene bottoms, solvent refined coal oils, shale oils, etc., provided only that such fuel is capable of producing hydrogen atoms or perhydroxal radicals when burned. There are some differences of opinion as to the mechanism of the reaction, i.e., whether as a result of the production of hydrogen atoms or perhydroxal radicals, but in any event, further reaction of the hydrogen or the perhydroxal radical with oxygen forms hydrogen peroxide. In addition to hydrogen peroxide, the reaction can produce varying amounts of carbon monoxide, carbon dioxide, hydrogen, water, unsaturated hydrocarbons, organic acids, ketones, aldehydes, ethers, esters, organic peroxides and alcohols, all of which, except alcohols, are also excellent materials for the control of microorganisms. However, it has been found, in accordance with the present invention, that, if the fuel-oxygen mixture is substantially below the stiochiometric ratio, to produce a fuel-lean mixture, and the residence time is extremely short, the production of hydrogen peroxide will be maximized. Specifically, the fuel/air equivalence ratio should be between about 0.1 and 0.6, and more preferably between about 0.1 and 0.2, and the residence time should be between about 1 and 10 milliseconds, and preferably between about 1 and 3 milliseconds.

The reaction should also be carried out at a relatively high temperature, preferably between about 800° and 1300° F., since, at this temperature, the production of hydrogen peroxide is increased at the expense of oxygenated organic materials. The maintenance of a proper temperature in the reactor can also be aided by preheating the air to temperatures between ambient temperature up to about 800° F. Where heavy, normally liquid fuels are utilized, it is also advantageous to preheat the fuel so that it can be readily atomized and mixed with the air. The temperature in the burining zone can also be controlled to a certain extent, by dilution of the fuel-air mixture with water. This also prevents undesirable side reactions such as cracking of the hydrocarbons.

Significant quantities of hydrogen peroxide can also be produced with fuel-oxygen ratios above the stoichiometric ratio, utilizing longer residence times and at lower temperatures. Under such conditions, the production of organic compounds, including aldehydes, increases, particularly at lower temperatures. On the other hand, at higher temperatures the concentration of hydrogen peroxide and olefins increases.

The fuel and air are preferably premixed prior to burning or combustion and suitable techniques for accomplishing this will be apparent from the description of the apparatus. In addition, it is highly desirable that the fuel and air pass through the combustion zone as an annularly stratified body with a fuel-rich core and an outer fuel-lean annular shell. Such stratification of the fuel-air mixture in the combustion zone has numerous advantages, including flame stabilization at the very high flow velocities hereinafter mentioned, protection of the walls of the combustion zone, as will be hereinafter detailed, and prevention of decomposition of the hydrogen peroxide, which is known to occur when certain materials, such as metals, are utilized for walls of the combustion zone.

As previously indicated, the burning should be carried out at a very high flow velocity, preferably above about 250 feet per second. If the burning proceeds too slowly, there is also a tendency for the hydrogen peroxide to decompose before the hereinafter mentioned termination of the reaction.

Where premixing of the fuel and air is performed in the apparatus prior to combustion, it is also desirable to prevent flashback of the flame into the mixing zone. This will be more apparent when reference is made to suitable apparatus for carrying out the present invention.

Another very critical factor in the operation of the present invention is the rapid termination of the reaction by, at least in part, injecting additional air and/or water into the flame front. This rapid termination or quenching prevents the reaction from reaching equilibrium and thus, decomposition of the hydrogen peroxide. The rapid termination or quenching is further aided by the manner of introducing the quenching fluid, for example, as a plurality of radially directed jets, also abruptly expanding the flame front immediately adjacent the point of introduction of the quenching fluid and, preferably, reducing the peripheral dimension of the flame front prior to such expansion and introducing the quench fluid before the reduction in dimension, in the reduced dimension portion of the flame front or immediately after reduction in the dimension of the flame front. The manner of doing this will also be explained in more detail in discussing the apparatus.

From the above it is obvious that operation in accordance with the present invention overcomes innumerable problems in connection with the production, handling and use of hydrogen peroxide as a microorganism control material.

The entire quenched effluent from the hydrogen peroxide generation step is then contacted with the body of fluid to be treated. In the case of a confined body of fluid in a tank or container, a pond or the like the effluent would be preferably passed through a distributing means so as to cause the effluent to bubble through the body of fluid. Where a flowing stream of fluid is to be treated, such as in a stream, it is preferable to utilized a distributing means and pass the fluid through the distributing means. On the other hand, if the fluid to be treated is flowing through a pipeline, down a wellbore or the like, all or part of the fluid to be treated can be utilized as a quench fluid in the generator, downstream from the quench point, or point of introduction of quench fluid in the generator, after discharge of the effluent from the generator or a combination of these, effecting mixing of all of the effluent and fluid to be treated adjacent the point of use. In some cases, fuels utilized to generate the hydrogen peroxide may contain significant amounts of sulfur, which, in the presence of water, will produce sulfuric acid. Also, thermal $NO_x$ is produced in high temperature combustion process and, to the extent that the fuel contains significant amounts of bound nitrogen, additional $NO_x$ is formed and in the presence of water, nitric acid will be formed. While such acids are highly corrosive and detrimental in most cases, it should be recognized that corrosion inhibitors can be added to overcome this problem. It is also known that $SO_2$ and $NO_x$ are undesirable atmospheric pollutants and very strict limits are placed upon the discharge of such pollutants to the atmosphere by the U.S. Environmental Protection Agency. The present invention has a distinct advantage in that any free $SO_2$ and $NO_x$ produced by the generator will not be discharged into the atmosphere and thus cause pollution. It has been found that these materials are for the most part absorbed by the fluid being treated and where the generator effluent is discharged into a subsurface earth formation, such as in the water flooding of an oil-bearing subsurface earth formation, the formation itself scrubs essentially all of the $NO_x$ from the fluids and most of the $SO_x$ from the fluids, with a small amount of $SO_x$ appearing in the produced liquids rather than in produced gases. In all cases, therefore, it is preferred that the hydrogen peroxide generator effluent be contacted with fluid to be treated immediately after generation of the effluent. In this manner, the previously mentioned problems of handling hydrogen peroxide, particularly the decomposition of hydrogen peroxide during use, in accordance with conventional practice, are avoided.

Where a subsurface earth formation is to be water flooded to displace oil and the water is to be treated with hydrogen peroxide generator effluent, this may be done by positioning the generator at the surface of the earth and passing the effluent through a wellhead and thence down the well to the formation to be treated, positioning the generator in the wellhead and passing the effluent down the well to the formation to be treated or positioning the generator down the wellbore at a point immediately adjacent the formation to be treated. In all cases, the water may be contacted with the effluent in any of the ways previously described. Where the generator is located at the surface of the earth or in the wellhead, it will be advantageous to quench the flame front with air, rather than water, pass the quenched effluent down tubing in the well and separately introduce water down the annulus between the tubing and the well casing. By operating in this manner, the problems of decomposition of the hydrogen peroxide and passing the same from the surface to the subsurface formation are substantially eliminated, since significant decomposition does not occur until the hydrogen peroxide contacts the water. In addition, the problems of handling hydrogen peroxide solutions, or the like, are also eliminated, even if a conventional operation were carried out in which the flooding water and the hydrogen peroxide were separately injected into the well and then mixed adjacent the formation to be treated. However, the much preferred method of operation is to lower the generator into the well bore, generate the hydrogen peroxide immediately adjacent the formation to be treated and contact the formation with the generated effluent, and, in some cases, additional water, substantially immediately after generation of the effluent. The obvious advantages of such an operation appear from the above discussion, but it should be emphasized that the elimination of problems with the generation of hydrogen peroxide, the handling of hydrogen peroxide, the known tendency of hydrogen peroxide to deteriorate and the problems of air pollution are significant. The fact that the effluent is at an elevated temperature and an elevated pressure are also quite distinct advantages, since it is known that destruction of microorganisms by biocides is enhanced at elevated temperatures and the elevated pressure will aid in forcing the water into and through the formation. Normally, the effluent and water are introduced into an injection well, then passed through the formation to be treated and are then produced from a production well.

While the effluent from the hydrogen peroxide generator will, in most cases, contain other by-products, such as those mentioned above, these materials will not adversely affect the recovery of oil from a subsurface formation. As a matter of fact, some may even aid in the recovery. Also, to the extent that these by-products are recovered with fluids produced after contacting the solid materials, they can be separated from the produced fluids and utilized for other purposes. For example, if propane or the like is utilized as a fuel or the fuel contains alkyl hydrocarbons, significant amounts of olefins are known to be produced. These olefins can be recovered and ultimately utilized as a fuel or for other purposes. The same applies to surface treatments of a body of fluid.

As previously indicated, a number of the disadvantages of wet oxidation can be overcome for such a combustion process, as utilized to produce oxygen-containing, partial oxidation products, in accordance with the present invention, for use in the control of microorganisms in a waterflooding operation. In this particular case, water containing the fuel may be introduced into one of the well tubing or the annular space between the tubing and the casing and the tubing or annular space between the tubing and casing thereby become the reactor. Since the subsurface formation to be waterflooded will generally be at a high pressure, the formation pressure will thus provide the high pressure necessary for wet oxidation. In addition, residence time can be attained within the tubing or the annular space between the tubing and the casing or in an enlarged section of the bore hole adjacent the formation to be waterflooded. The oxidizing agent will be introduced at the top of the well, at the bottom or at some intermediate point as desired. Usually it would be introduced at the top of the well so that the long residence time for wet oxidation would be attained.

By way of illustration, partial oxidation of propane with air in a high intensity combustor utilizing water as a quench fluid under conditions to produce maximum amounts of hydrogen peroxide, one would expect the following reaction to occur.

$100C_3H_8 + 41\tfrac{1}{2}O_2 \longrightarrow 70C_3H_8 + 15C_3H_6 + C_2H_6 + 2C_2H_4 +$ $CH_4 + 13CO + 2CO_2 + 15H_2O_2 + 24H_2O + 3CH_3OH +$

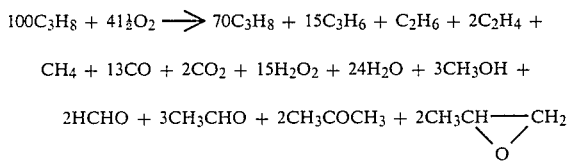

Disregarding the content of unreacted propane and air, along with nitrogen, carbon monoxide, carbon dioxide and other hydrocarbon products in the effluent, the effluent product would be expected to have the following composition of oxygen-containing partial oxidation products.

TABLE 1

| Moles | Component | Wt. % | Vol. % |
|---|---|---|---|
| 15 | Hydrogen Peroxide | 51.0 | 36.9 |
| 3 | Methyl Alcohol | 6.6 | 8.7 |
| 2 | Formaldehyde | 6.0 | 7.6 |
| 3 | Acetaldehyde | 13.2 | 17.5 |
| 2 | Acetone | 11.6 | 15.2 |
| 2 | Propylene Oxide | 11.6 | 14.1 |

TABLE 1-continued

| Moles | Component | Wt. % | Vol. % |
|---|---|---|---|
| 27 | | 100.0 | 100.0 |

Thus if desired, it is obvious that concentrations as high as 15 mol percent hydrogen peroxide can be obtained if desired and the total of microorganism control material present (excluding alcohol) would be about 24 mol percent. These amounts of microorganism control material when diluted by the microorganism containing fluid, which is to be treated, are more than adequate to control microorganisms.

In order to illustrate the effectiveness of the microorganism control material referred to above, a mixture of the oxygen-containing partial oxidation products in the above table was synthesized in the laboratory and this synthetic mixture was tested to determine biocidal effectiveness in a standard time kill test in sea water. The treated water contained 10% sulfate reducing bacteria. The following table shows the biocide concentration and the contact times for the synthesized partial oxidation products compared with a commercially available 50% glutaraldehyde biocide.

TABLE II

BIOCIDAL EFFECTIVENESS IN STANDARD TIME KILL TEST IN SEA WATER

| | Biocide Conc. | Contact Time | | | |
|---|---|---|---|---|---|
| | | 15 min | 30 min | 1 hour | 2 hours |
| Synthesized Biocide* | 100 ppm | + | − | − | − |
| | 500 ppm | − | − | − | − |
| 50% Glutaraldehyde | 10 ppm | + | + | + | + |
| | 50 ppm | + | − | − | − |

+ growth after 28 days
− no growth after 28 days
*Not tested at lower concentration It is to be observed from the above that the microorganism control composition in accordance with the present invention is quite effective in controlling sulfate reducing bacteria. While partial oxidation products of the present invention were utilized in higher concentrations than the glutaraldehyde, it should be recognized that the amounts of biocide utilized in accordance with the present invention are well within concentrations that can be produced by partial oxidation. In addition, it is believed that lower concentrations of the partial oxidation products would be equally effective and, even if not effective in the same concentrations as glutaraldehyde, practice of the present invention will result in substantial savings in costs and eliminate the problems of transporting and handling of commercial materials such as glutaraldehyde. It should also be noted that the sea water treated in the present invention is a simulated sea water under consideration for waterflooding an offshore oil formation. As previously indicated, aldehydes, such as formaldehyde and acetaldehyde are also higly effective microorganism control agents. Accordingly, partial combustion can be controlled to maximize aldehyde production. As is also previously indicated, this can be accomplished by utilizing higher molecular weight hydrocarbons as a fuel, for example, crude oil, and utilizing a longer residence time, to attain larger yields of low molecular weight aldehydes and formaldehyde.

In order to illustrate the cost advantage of the present invention versus use of a conventional biocide in a waterflooding operation, an economic analysis was made. In this analysis, it was assumed that one part of crude oil would be burned under conditions to produce maximum volumes of aldehyde. It was further assumed that the oil and air would be preheated to about 700° F. Under these circumstances, it was estimated that one part of oil plus one part of air would yield three parts of water containing about 3% of low molecular weight aldehydes. If 90% of the unburned oil were ultimately recovered, it was found that the cost ratio of the previously mentioned glutaraldehyde compared with the thus produced microorganism control agent would be about 35.1 to 1. Further, even if none of the unburned oil were recovered, which is unlikely, it was found that a cost ratio of 4.6 to 1 could still be obtained.

The present invention will be further illustrated by a reference to the drawings which show a preferred apparatus useful in accordance with the present invention.

FIG. 1 of the drawings illustrates the basic structure of a microorganism control material generator used in accordance with the present invention. The apparatus of FIG. 1 is designed for the use of a normally gaseous fuel. The apparatus basically comprises a mixing zone 2, a combustion zone 4, a quench or cooling chamber 6 and a discharge nozzle 8. Fuel is introduced through fuel introduction means 10 as a generally axial stream into mixing zone 2. Air is introduced into the mixing zone 2 through an appropriate swirl means 12. Swirl means 12 can be any of the well known means for creating a swirling annular stream of air, such as an annular ring with fins at appropriate angles, a plurality of peripheral, tangential introduction ports or the like. The fuel and air are partially mixed in mixing zone 2 and are then passed through barrier means 14. Barrier means 14 is a suitable perforated grid, which together with the axial introduction of the fuel and the annular introduction of the air creates an annularly stratified body of fluids, which is fuel-rich along the axis of combustion zone 4 and fuel-lean adjacent the walls of combustion zone 4. Such stratification prevents the body of fluids from reaching equilibrium oxygen atom concentrations before reaching the quench zone. In addition, the grid absorbs heat and prevents flashback of the flame into fuel-air mixing zone 2. Additionally, this stabilizes the flame in combustion zone 4 at the very high flow velocities employed in accordance with the present invention. Grid 14 also increases the flow velocity. The generator of FIG. 1 is designed for the use of natural gas as a fuel and, accordingly, combustion zone 4 is approximately 3 inches in length and three inches in diameter to attain the previously mentioned short residence time. Ignition of the fuel-air mixture is effected by spark plug 16. Quench fluid, in the case illustrated water, is introduced through line 18, passes through annular chamber 20 in indirect heat exchange with the combustion zone, thence, into annular plenum 22 and finally is introduced into the flame front through a plurality of annularly spaced apertures 24. Utilization of the quench fluid in indirect heat exchange with the combustion zone 4, at least in part, permits the utilization of a metal combustion chamber as opposed to a ceramic lined combustion chamber. A ceramic lined chamber might be fractured under the conditions employed in accordance with the present invention. In addition, the use of a metallic combustion chamber permits one to construct a generator having a relatively small diameter, in the case illustrated about six inches in diameter. In the apparatus shown, the quench fluid, in passing into the flame front as a plurality of radial jets, aids in the mixing of the quench fluid with the flame front and thus the abrupt termination of the reaction. In addition, the quench fluid is injected in the vena contracta of a nozzle 26. Nozzle 26 serves to reduce the diameter of the flame front and thereafter expand the same. This reduction and abrupt expansion aid the mixing of the quench fluid with the flame front and also prevent back flow of the quench fluid into the combustion zone. It should be recognized that the quench fluid also can be introduced immediately before or immediately after the vena contracta. It should also be recognized that the angle of expansion can be varied within certain limits, in accordance with the present invention. This will be explained in more detail with reference to FIG. 3. A cooled or quenched effluent is then passed to a chamber of suitable dimensions to permit the mixture to achieve a product of uniform composition and velocity. Exhaust nozzle 8 may not be necessary in all cases, since its primary function is to produce a product of uniform composition and velocity. However, nozzle 8 could serve as a mixing nozzle for the addition of chemicals or the introduction of all or part of the fluid to be treated, by introducing the chemicals or the water immediately before, into, or immediately after the vena contracta of the nozzle 8.

As previously indicated, the generator of FIG. 1 is designed to have a maximum diameter of about six inches. This has the advantage of providing a structure capable of safely operating under the conditions utilized herein. In addition, the generator of FIG. 1 can be readily utilized in a conventional well bore having a casing seven inches in diameter, which is a standard size. It is also possible to construct the generator so as to have a diameter of about twelve inches to thereby fit into a well having a casing of thirteen inches in diameter. In the latter instance, the severe space limitations of a seven-inch casing do not exist and the generator can be designed without indirect cooling by the quench fluid and instead utilizing a conventional blanket-type insulation. It is also possible in this case to utilize a ceramic lined combustion zone.

A modification of the generator of FIG. 1 is shown in FIG. 2. In FIG. 2, fuel and air are introduced through lines 10 and 28, respectively, as previously described and are introduced as opposed radial jets to achieve a momentum-density balance and thus mixing at their plane of intersection. However, air line 28 is provided with an appropriate spray head 30, which produces a shower head-type effect as the air contacts the fuel. Also, the premixed fuel and air then passes through an orifice 32 which further aids in the mixing by reducing the diameter of the mixture and then abruptly expanding the mixture at an angle of 90° with respect to the wall of the combustion chamber 4. This contraction and abrupt expansion of the mixture also prevents feedback into the mixing chamber 2. Quench fluid is introduced through line 18 and is not utilized as an indirect cooling medium for chamber 4, but instead, passes directly into annular plennum 34 and thence through apertures 36 into the flame adjacent the downstream end of combustion chamber 4. Accordingly, introduction of the quench fluid as a plurality of annularly spaced radial jets performs the function of abruptly terminating the combustion and mixing the quench fluid with the fluids in the flame front. Also, in this configuration, the combustion chamber is surrounded by an appropriately insulated shell 38. The quenched or cooled effluent then passes through chamber 6 and through nozzle 8 in essentially the same manner as in FIG. 1.

Figure 3:
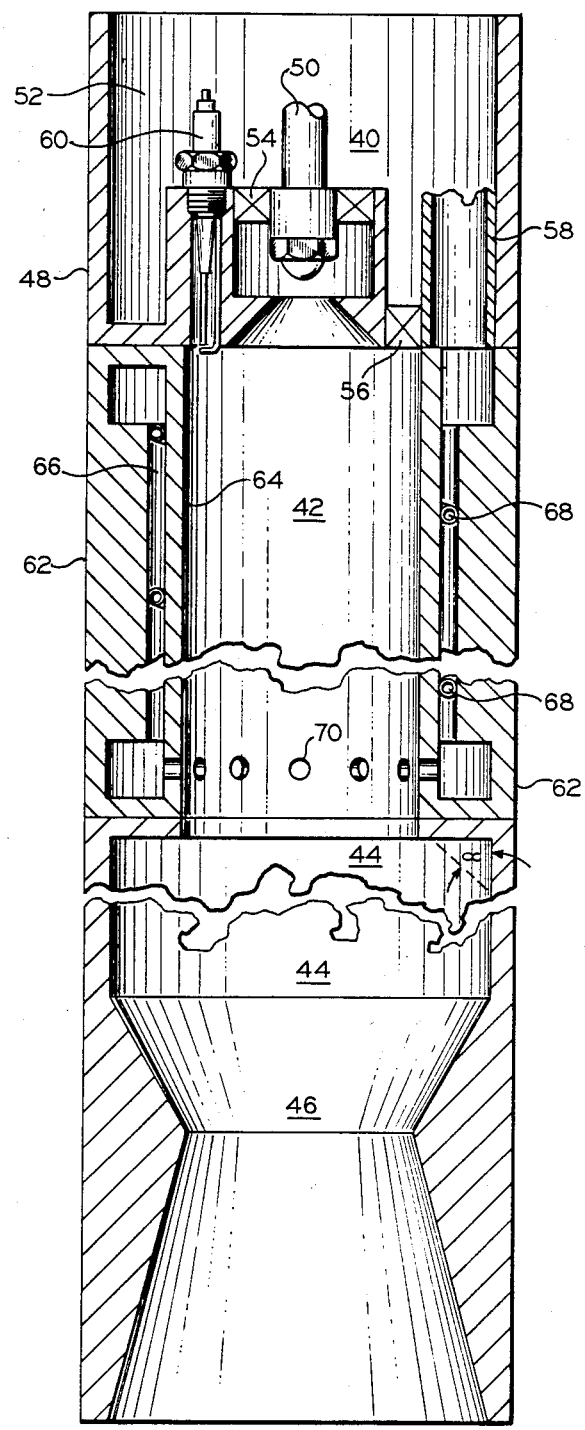
FIG. 3 is a schematic view, partially in cross section, of another modification of the generator of FIG. 1.

FIG. 3 of the drawings shows a generator suitable for use when a normally liquid fuel is utilized.

The generator comprises four basic sections or modules, namely, a combustor head 40, a combustion chamber 42, a mixing chamber 44 and an exhaust nozzle 46. All of the modules are connected in a manner such that they are readily separable for the substitution of alternate subunits, servicing, repair, etc. In some cases, however, the combustion chamber 42 and mixing chamber 44 can be permanently connected subunits, since the unit can be designed so that these two subunits can be utilized for most types of fuel and most water injection rates. In certain instances it may also be desirable to substitute a different exhaust nozzle or a different fuel introduction means. The head 40 has a body portion or outer casing 48. A fuel introduction means 50 is mounted along the axis of casing 48 to introduce fuel centrally and axially into the combustion chamber 42. In the particular instance schematically shown herein, the fuel introduction means 50 is an atomizing nozzle adapted for the introduction of a liquid fuel. Such atomizing nozzles are well known in the art and the details thereof need not be described herein. However, the nozzle may be any variety of spray nozzles or fluid assist nozzles, such as an air assist or steam assist nozzle. Obviously, an air assist nozzle, where such assistance is necessary, is preferred if there is no readily available source of steam. This is particularly true where the unit is utilized downhole and surface steam is not readily available. In any event, the nozzle 50 sprays the appropriately atomized liquid fuel in a diverging pattern into the combustion chamber 42. Combustion supporting gas, particularly air, is introduced into a plenum chamber 52 formed within outer casing 48. Obviously, the plenum chamber 52 can be separated into two or more separate plenum chambers for introducing separate volumes of air, as hereinafter described. It is also possible to supply more than one volume of air through separate lines from the surface. This, of course, would provide separate control over each of a plurality of volumes of air beyond that controlled by the cross-sectional area of the air openings in each specific case. It is also possible that each of the air entries to the combustion chamber could be constructed to vary the cross-sectional area of air openings and could be remotely controlled in accordance with techniques known to those skilled in the art. In any event, a first volume of air is introduced around nozzle 50 through a swirler 54. Swirler 54 may be any appropriate air introduction swirler which will introduce the air in a swirling or rotating manner, axially into the combustion chamber 42 and in a downstream direction. The specific variations would include a plurality of fins at an appropriate angle, such as 45° (apex angle of 90°), or a plurality of tangentially disposed inlet channels. In any event, the air then enters combustion chamber 42 as a swirling or rotating annular body, rotating in a clockwise or counterclockwise direction. A second air swirler 56 is formed adjacent the inner wall of combustion chamber 42 and is of essentially the same construction as swirler 54. Swirler 56, in like manner to 54, introduces the air as a swirling or rotating annular body of air along the inner wall of combustor chamber 42. The rotation of the air by swirler 52 and swirler 54 are in opposite directions. Specifically, if the air is rotated in a clockwise direction by swirler 52, it should be rotated in a counterclockwise direction by swirler 54. This manner of introducing the air through swirlers is extremely important in the operation of the unit of the present invention, particularly where fuels having a tendency to deposit carbon and tar on hot surfaces are utilized, and to prevent burning of the combustion chamber walls. Also introduced through combustor head 40 is water, through water inlet 58. Also mounted in the combustor head is a suitable lighter or ignition means 60. In the present embodiment, igniter means 60 is a spark plug. However, where fuels having high ignition temperatures are utilized, the igniter means may be a fuel assisted ignition means, such as a propane torch or the like which will operate until ignition of the fuel/air mixture occurs. In some cases, a significant amount of preheating of the fuel or fuel-air mixture is necessary.

The combustion chamber includes an outer casing 62 and an inner burner wall 64, which form an annular water passage 66 therebetween. Water passage 66 is supplied with water through water conduit 58 and cools the combustion chamber. This external cooling with water becomes a significant factor in a unit for downhole operation, since, in some cases, for example where the tool is to be run in a casing with an internal diameter of about 7 inches, the tool itself will have a diameter of 6 inches. This small diameter does not permit mechanical insulation of the combustion chamber and, accordingly, effective cooling is provided by the water. It should be recognized at this point that transfer of heat from the combustion chamber to the water in passage 66 is not necessary. In order to prevent the formation of air bubbles or pockets in the body of cooling water, particularly toward the upper or upstream end of the channel, water swirling means 68 is spirally found in the water channel 66 to direct the water in a spiral axial direction through the channel. The water swirling means 68 can be a simple piece of tubing or any other appropriate means. A primary concern in the operation of the generator is combustion cleanliness, that is the prevention of deposits on the wall of the combustion chamber and production of soot emmissions as a result of incomplete combustion. This becomes a particular problem where heavy fuels are utilized and the problem is aggravated as combustor pressure increases and/or combustion temperature decreases. In any event, the manner of introducing the air into the generator substantially overcomes this problem. The counter rotating streams of air in the combustion chamber provide for flame stabilization in the vortex-flow pattern of the inner swirl with intense fuel-air mixing at the shear interface between the inner and outer streams of air for maximum fuel vaporization. Also, this pattern of air flow causes fuel-lean combustion along the combustion chamber walls to prevent build up of carbonacious deposits, soot, etc. Following passage of the water through channel 66, the water is injected into the combustion products or flue gases from combustion chamber 42 through appropriate holes or apertures 70. Another extremely important factor, in the operation of the generator of the present invention, is the prevention of feedback of excessive amounts of quench fluid or water from the mixing section 44 into the combustion section 42, because of the chilling effect which such feedback would have on the burning of the soot particles which are produced during high pressure combustion. Such feedback is prevented by the axial displacement of the vortex flow patterns from the counter rotational air flow. Another extremely important factor in the operation of the steam generator is the manner of introduction of quench fluid or water into the flue gas. In accordance with the present invention, such introduction is accomplished by introducing the water as radial jets into the flue gases, such jets preferably penetrating as close as possible to the center of the body of combustion products. The combustion products—quench fluid or—water mixture is then abruptly expanded as it enters mixing chamber 44. Accordingly, substantially complete mixing will occur and the formation of water droplets or water slugging in the mixture will be eliminated. Abrupt expansion in the present case is meant to include expansion at an angle (alpha) significantly greater than 15°, since expansion is about 15° causes streamline flow or flow along the walls rather than reverse mixing at the expander. By the time the mixture of combustion products and quench fluid or water reach the downstream end of mixing chamber 44, substantially complete mixing is attained.

Figure 4:
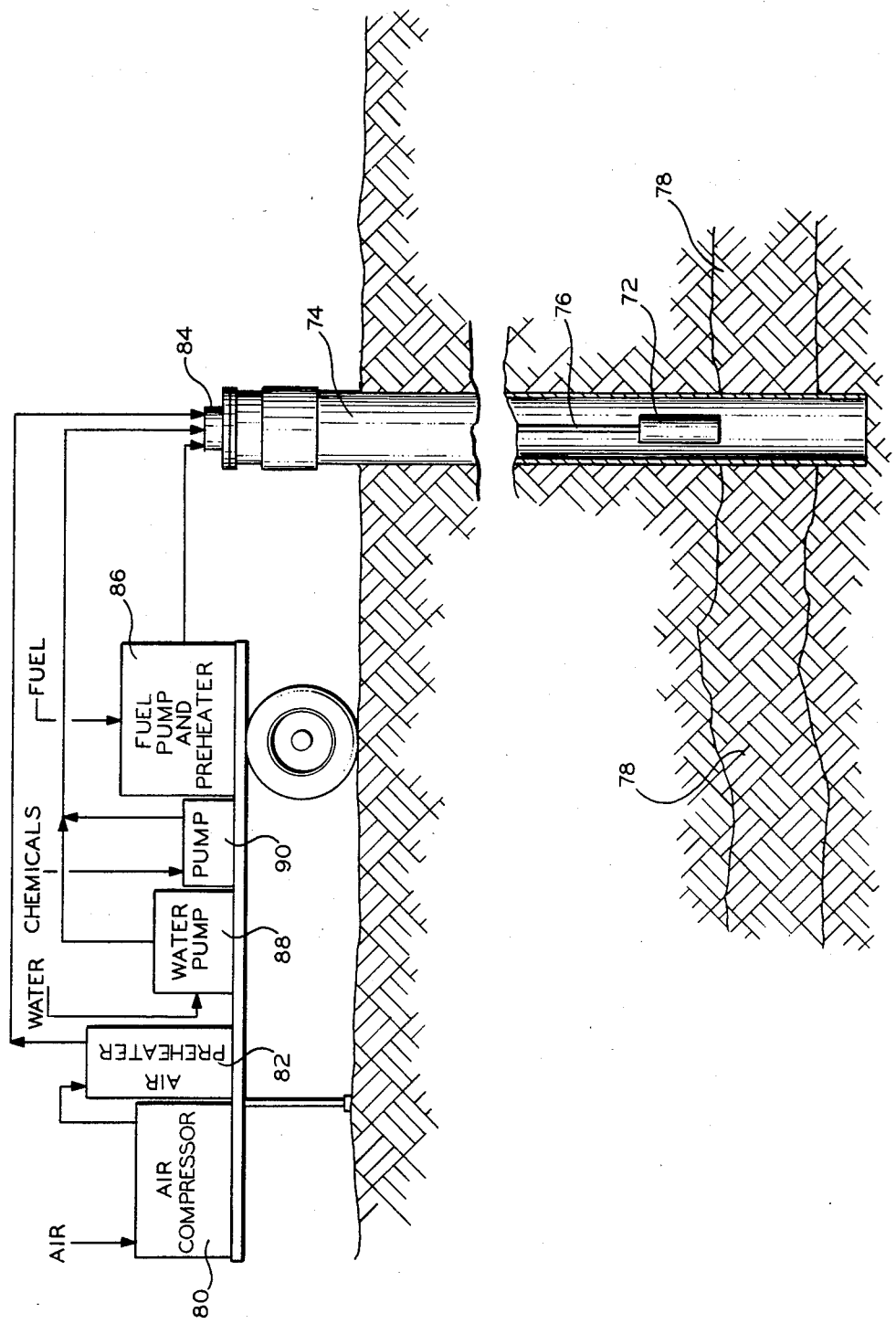
FIG. 4 is an elevational view, partially in cross section, showing equipment for utilizing the present invention in treating subsurface earth formations.

FIG. 4 illustrates support equipment for the operation of the generator of the present invention and illustrates the use of the generator down a wellbore for water flooding an oil-bearing subsurface formation. The support equipment may be mounted on a mobil unit, as shown, or it can be stationary. In addition, economics may dictate that a centralized battery of support equipment or a centralized support unit is provided to supply compressed air to the plurality of different injection wells.

In accordance with FIG. 4 the generator 72 is suspended in casing 74 by an umbilical 76. As illustrated, generator 72 is disposed adjacent subsurface formation 78, which is to be flooded and, therefore, will discharge the effluent from the generator substantially directly into subsurface formation 78. Air for the operation of the generator is supplied to an appropriate air compressor 80. The compressed air is then passed to an air preheater 82, where such preheating is desired, which preheats the air to an appropriate temperature for use in a generator. Compressed air is then fed to the generator 40 through well head 84 connected to the top of casing 74. Fuel is introduced through an appropriate pump or fuel pump and preheater 86, depending upon the nature of the fuel. Where the fuel is a normally gaseous fuel, such as natural gas, fuel pump and preheater 86 would be replaced by an appropriate compressor if the gas is not already at an appropriate pressure for use in the generator. The fuel from fuel pump and preheater 86 is then passed to tht well head 84. Flooding water is introduced to water pump 88 and from the water pump to the well head 84. Where chemicals, such as corrosion inhibitors are to be added to the water, such chemicals can be supplied from a pump 90 and into the water line to well head 84.

As previously pointed out, utilizing the effluent from the generator to kill microorganisms in bodies of fluid such as tanks, ponds and the like is effective for killing the microorganisms. However, where the effluent is mixed with flooding water utilized to displace oil from a subsurface oil-bearing formation, the materials of the effluent which are normally inert in other applications are of value and actually improve the displacement of the oil over a simple water injection operation. For example, the carbon dioxide created during the generation process is absorbed by the oil and increases its mobility without expending additional energy. The nitrogen also contributes to a high velocity drag which increases both crude oil production rate and efficiency.

As a matter of fact, in some instances, depending upon the nature of the reservoir, the nitrogen can actually create an artificial gas cap and thus apply additional pressure for oil displacement. In addition, since the effluent is at a high pressure, additional pressure for displacement of the oil is supplied, again without expending additional energy, and/or the pressure required for forcing the water through the reservoir can be accordingly reduced. Further, the high temperature of the effluent also contributes to increased oil recovery, particularly if the oil to be displaced is highly viscous.

Figure 5:
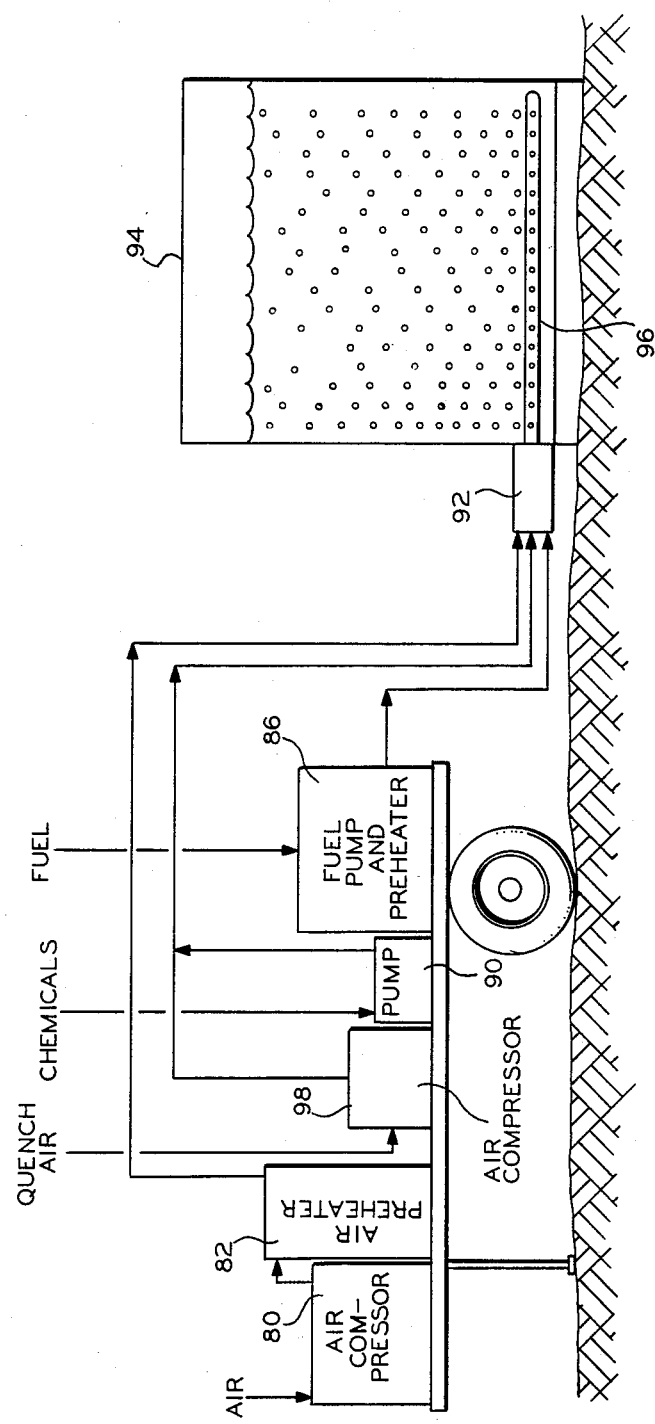
FIG. 5 is an elevational view, partially in cross section, showing equipment for utilizing the present invention in treating a confined body fluid.

FIG. 5 of the drawings shows a support equipment arrangement similar to that of FIG. 4. To the extent that the same items of equipment are shown in FIGS. 4 and 5, the same reference numerals are utilized. In accordance with FIG. 5, effluent from generator 92 is passed through a body fluid disposed in a tank 94 through distributor means 96. While water can be utilized as a quench fluid in generator 92 in the same manner as shown in FIG. 4 of the drawings, in this particular case, it is preferable to quench the effluent in generator 92 with additional air. For this purpose, quench air is supplied to air compressor 98 and thence to generator 92. Treating chemicals may be dispersed in the additional air in the same manner as they are mixed with the water in FIG. 4 or they may be added as a liquid solution downstream of the quenching point in generator 92, or simply, to the fluid in tank 94.

While specific materials, specific items of equipment and specific conditions of operation have been set forth herein, it is to be understood that such specifics are by way of illustration only, and the present invention is not to be limited in accordance with such recitals.

That which is claimed:

1. A method of treating a body of fluid containing microorganisms to kill said microorganisms, comprising:
   (a) burning a hydrogen-containing fuel within a reactor in the presence of oxygen under conditions sufficient to produce a flame front containing significant amounts of hydrogen peroxide;
   (b) abruptly terminating said burning to prevent significant decomposition of the thus produced hydrogen peroxide and the formation of other products therefrom, by, at least in part, introducing a quench medium into said flame front within the said reactor to produce a hydrogen peroxide-containing effluent; and
   (c) contacting said body of fluid with said hydrogen peroxide-containing effluent.

2. A method in accordance with claim 1 wherein the quench medium is one of air, water and air plus water.

3. A method in accordance with claim 1 wherein the amount of oxygen during the burning step is below the stoichiometric amount necessary to burn all of the fuel.

4. A method in accordance with claim 3 wherein the equivalance ratio during the burning step is between about 0.1 and 0.2.

5. A method in accordance with claim 1 wherein the temperature during the burning step is maintained between about 800° and about 1300° F.

6. A method in accordance with claim 1 wherein the residence time of the burning step is between about 1 and about 10 milliseconds.

7. A method of treating a body of liquid containing microorganisms to kill said microorganisms, comprising:

(a) burning a hydrogen-containing fuel in the presence of oxygen under conditions sufficient to produce a flame front containing significant amounts of hydrogen peroxide;

(b) abruptly terminating said burning to prevent significant decomposition of the thus produced hydrogen peroxide and the formation of other products therefrom, by, at least in part, introducing at least a portion of said body of liquid into said flame front to produce a hydrogen peroxide-containing effluent; and (c) contacting the remaining portion of said body of liquid, if any, with said hydrogen peroxide-containing effluent.

8. A method in accordance with claim 7 wherein the body of liquid is an aqueous fluid.

9. A method in accordance with claim 7 wherein the amount of oxygen during the burning step is below the stoichiometric amount necessary to burn all of the fuel.

10. A method in accordance with claim 9 wherein the equivalence ratio during the burning step is between about 0.1 and 0.2.

11. A method in accordance with claim 7 wherein the temperature during the burning step is maintained between about 800° and about 1300° F.

12. A method in accordance with claim 7 wherein the residence time of the burning step is between about 1 and about 10 milliseconds.

13. A method of displacing oil from a subsurface earth formation, penetrated by at least one borehole, with a body of aqueous fluid containing microorganisms and to simultaneously control said microorganisms, comprising:

(a) burning a hydrogen-containing fuel within a reactor in the presence of oxygen under conditions sufficient to produce a flame front containing significant amounts of hydrogen peroxide;

(b) abruptly terminating said burning to prevent significant decomposition of the thus produced hydrogen peroxide and the formation of other products therefrom, by, at least in part, introducing a quench medium into said flame front within said reactor and to produce a hydrogen peroxide-containing effluent;

(c) treating said body of aqueous fluid with said hydrogen peroxide-containing effluent by at least one of (1) mixing said hydrogen peroxide-containing effluent and at least part of said body of aqueous fluid at the surface of the earth, (2) mixing said hydrogen peroxide-containing effluent and at least a part of said body of aqueous fluid in the top of said borehole, (3) mixing said hydrogen peroxide-containing effluent with at least part of said body of aqueous fluid in said borehole adjacent said subsurface earth formation and (4) introducing at least part of said body of aqueous fluid into said flame front as at least a part of said quench medium to produce a mixture of all of said hydrogen peroxide-containing effluent and all of said body of aqueous fluid within said subsurface earth formation; and (d) displacing the thus produced mixture of hydrogen peroxide-containing effluent and said body of aqueous fluid through said subsurface earth formation.

14. A method in accordance with claim 13 wherein the burning is carried out at the surface of the earth.

15. A method in accordance with claim 13 wherein the burning is carried out in the top of the borehole.

16. A method in accordance with claim 13 wherein the burning is carried out in the borehole adjacent the subsurface earth formation.

17. A method in accordance with claim 13 wherein the amount of oxygen present during the burning step is below the stoichiometric amount necessary to burn all of the fuel.

18. A method in accordance with claim 17 wherein the fuel/oxygen equivalence ratio during the burning step is between about 0.1 and 0.2.

19. A method in accordance with claim 13 wherein the temperature during the burning step is maintained between about 800° and 1300° F.

20. A method in accordance with claim 13 wherein the residence time of the burning step is between about 1 and about 10 milliseconds.

21. A method of treating a body of fluid containing microorganisms to control said microorganisms comprising:

(a) burning a hydrogen-containing fuel within a reactor in the presence of an oxidizing agent under conditions sufficient to produce partial oxidation products containing significant amounts of at least one compound capable of controlling microorganisms;

(b) abruptly terminating said burning to prevent significant decomposition of the thus produced partial oxidation products and the formation of products of complete combustion therefrom, by, at least in part, introducing a quench fluid into said partial oxidation products within said reactor to produce an effluent containing said partial oxidation products; and (c) contacting said body of fluid with said effluent containing said partial oxidation products.

22. A method in accordance with claim 21 wherein the compound capable of controlling microorganisms and thus contained within said partial oxidation products is a material selected from the group consisting of hydrogen peroxide, aldehydes, ketones, ethers, esters and organic peroxides.

23. A method in accordance with claim 22 wherein the quench medium is at least a part of the body of fluid being treated.

24. A method in accordance with claim 21 wherein the burning is carried out under conditions to maximize the amount of at least one of hydrogen peroxide, aldehydes, ketones, ethers, esters and organic peroxides, as the compound capable of controlling microorganisms and thus contained within said partial oxidation products.

25. A method in accordance with claim 24 wherein the burning is carried out under conditions to maximize the amount of aldehydes thus contained within the partial oxidation products.

26. A method of treating a body of fluid containing microorganisms to control said microorganisms comprising:

(a) burning a hydrogen-containing fuel within a reactor in the presence of an oxidizing agent under conditions sufficient to produce partial oxidation products containing significant amounts of at least one compound capable of controlling microorganisms;

(b) abruptly terminating said burning to prevent significant decomposition of the thus produced partial oxidation products and the formation of other products therefrom, by, at least in part, introducing a quench fluid into said flame front within said reactor to produce an effluent containing said partial oxidation products;

(c) maximizing the amount of said compound capable of controlling microorganisms thus contained within said partial oxidation products by at least one of (1) utilizing a particular type of said hydrogen-containing fuel in said burning, (2) maintaining a particular fuel/oxidizing agent equivalence ratio during said burning, (3) maintaining a particular temperature during said burning, (4) maintaining a particular pressure during said burning, and (5) carrying out said burning for a particular residence time; and (d) contacting said body of fluid with said effluent containing partial oxidation products.

27. A method in accordance with claim 26 wherein the compound capable of controlling microorganisms and thus contained within said partial oxidation products is a material selected from the group consisting of hydrogen peroxide, aldehydes, ketones, ethers, esters and organic peroxides.

28. A method in accordance with claim 26 wherein the burning is carried out under conditions to maximize the amount of at least one of hydrogen peroxide, aldehydes, ketones, ethers, esters and organic peroxides, as the compound capable of controlling microorganisms and thus contained within said partial oxidation products.

29. A method in accordance with claim 28 wherein the burning is controlled to maximize the amount of aldehydes thus contained within the partial oxidation products.

30. A method in accordance with claim 26 wherein the quench medium is at least part of the body of fluid being treated.

31. A method of displacing oil from a subsurface earth formation, penetrated by at least one borehole, with a body of aqueous fluid containing microorganisms and to simultaneously control said microorganisms comprising:

(a) burning a hydrogen-containing fuel within a reactor under conditions sufficient to produce an effluent including partial oxidation products containing significant amounts of at least one compound capable of controlling microorganisms;

(b) abruptly terminating said burning to prevent significant decomposition of the thus produced partial oxidation products and the formation of other products therefrom, by, at least in part, introducing a quench fluid into said flame front within said reactor to produce an effluent containing said partial oxidation products;

(c) treating said body of aqueous fluid by one of (1) mixing said effluent containing partial oxidation products and at least part of said body of aqueous fluid at the surface of the earth, (2) mixing said effluent containing partial oxidation products and at least part of said body of aqueous fluid in the top of said borehole, (3) mixing said effluent containing partial oxidation products and at least part of said body of aqueous fluid in said borehole adjacent said subsurface earth formation and (4) introducing at least part of said body of aqueous fluid into said flame front as at least part of said quench fluid to produce a mixture of all of said effluent containing partial oxidation products and said body of aqueous fluid within said subsurface earth formation; and (d) displacing the thus produced mixture of said effluent including partial oxidation products and said aqueous fluid through said subsurface earth formation.

32. A method in accordance with claim 31 wherein the compound capable of controlling microorganisms and thus contained within said partial oxidation products is a material selected from the group consisting of hydrogen peroxide, aldehydes, ketones, ethers, esters and organic peroxides.

33. A method in accordance with claim 31 wherein the burning is carried out under conditions to maximize the amount of at least one of hydrogen peroxide, aldehydes, ketones, ethers, esters and organic peroxides, as the compound capable of controlling microorganisms and thus contained within said partial oxidation products.

34. A method in accordance with claim 33 wherein the burning is carried out under conditions to maximize the amount of aldehydes thus contained within the partial oxidation products.

35. A method in accordance with claim 31 wherein the quench medium is at least part of the body of fluid being treated.

36. A method in accordance with claim 31 wherein the burning is carried out at the surface of the earth.

37. A method in accordance with claim 31 wherein the burning is carried out in the top of the borehole.

38. A method in accordance with claim 31 wherein the burning is carried out in the borehole adjacent the subsurface earth formation.

* * * * *